(12) United States Patent
Bell, Jr. et al.

(10) Patent No.: US 9,974,452 B2
(45) Date of Patent: May 22, 2018

(54) INDUCTIVE NON-CONTACT RESISTANCE MEASUREMENT

(71) Applicant: SYNAPTICS INCORPORATED, San Jose, CA (US)

(72) Inventors: Marshall J. Bell, Jr., Dripping Springs, TX (US); Jeffrey S. Lillie, Mendon, NY (US)

(73) Assignee: SYNAPTICS INCORPORATED, San Jose, CA (US)

( * ) Notice: Subject to any disclaimer, the term of this patent is extended or adjusted under 35 U.S.C. 154(b) by 173 days.

(21) Appl. No.: 14/983,241

(22) Filed: Dec. 29, 2015

(65) Prior Publication Data

US 2017/0181650 A1    Jun. 29, 2017

(51) Int. Cl.
| | |
|---|---|
| *G01R 27/28* | (2006.01) |
| *A61B 5/024* | (2006.01) |
| *A61B 5/02* | (2006.01) |
| *A61B 5/08* | (2006.01) |
| *A61B 5/026* | (2006.01) |
| *A61B 5/00* | (2006.01) |
| *A61B 5/053* | (2006.01) |

(52) U.S. Cl.
CPC .......... *A61B 5/02444* (2013.01); *A61B 5/026* (2013.01); *A61B 5/02007* (2013.01); *A61B 5/053* (2013.01); *A61B 5/08* (2013.01); *A61B 5/6825* (2013.01); *A61B 5/0816* (2013.01); *A61B 5/6824* (2013.01); *A61B 5/7225* (2013.01); *A61B 2560/0214* (2013.01); *A61B 2562/0214* (2013.01)

(58) Field of Classification Search
CPC .... G01R 33/04; G01R 15/207; G01R 33/072; G01R 33/09
USPC .............................. 324/253, 200, 207.3, 244
See application file for complete search history.

(56) References Cited

U.S. PATENT DOCUMENTS

| | | | |
|---|---|---|---|
| 6,359,449 | B1 | 3/2002 | Reining et al. |
| 7,254,439 | B2 | 8/2007 | Misczynski et al. |
| 7,638,341 | B2 | 12/2009 | Rubinsky et al. |
| 8,361,391 | B2 | 1/2013 | Rubinsky et al. |
| 8,655,272 | B2 | 2/2014 | Saunamaki |
| 8,754,609 | B2 | 6/2014 | Tsai et al. |

(Continued)

FOREIGN PATENT DOCUMENTS

| | | |
|---|---|---|
| WO | 1998048693 A1 | 11/1998 |
| WO | 2014096043 A2 | 6/2014 |

*Primary Examiner* — Giovanni Astacio-Oquendo
(74) *Attorney, Agent, or Firm* — Paradice and Li LLP

(57) ABSTRACT

Embodiments herein describe a user device that includes a dual purpose coil (or inductor) used when performing inductive sensing and when transferring electrical power to the user device. When performing inductive sensing, the user device couples the coil to a sensing circuit which measures a resistivity of a lossy material inductively coupled to the coil. In one embodiment, the user device may be worn on the wrist of the user so that the sensing circuit measures the resistivity corresponding to the flow of blood in an artery or vein. By monitoring changes in the resistivity of the blood or artery, the user device can identify the heartbeat of the user. When transferring electrical power, the user device couples the coil to a charging circuit which receives the power provided by an external charging device that is inductively coupled to the coil.

20 Claims, 5 Drawing Sheets

(56) References Cited

U.S. PATENT DOCUMENTS

| | | | |
|---|---|---|---|
| 2002/0165584 A1* | 11/2002 | Moore | A61N 1/08 607/2 |
| 2004/0213140 A1* | 10/2004 | Taylor | G09B 5/02 369/292 |
| 2005/0148894 A1 | 7/2005 | Misczynski et al. | |
| 2006/0217906 A1* | 9/2006 | Barbara | G01R 1/36 702/60 |
| 2008/0309466 A1* | 12/2008 | Zhao | B06B 1/0215 340/384.7 |
| 2010/0281854 A1* | 11/2010 | Huang | F02D 41/1495 60/276 |
| 2012/0182023 A1* | 7/2012 | Zhang | G01M 11/3109 324/501 |
| 2014/0275912 A1 | 9/2014 | Gu et al. | |

* cited by examiner

INDUCTIVE NON-CONTACT RESISTANCE MEASUREMENT

FIELD OF THE INVENTION

This invention generally relates to electronic devices.

BACKGROUND OF THE INVENTION

Input devices including proximity sensor devices (also commonly called touchpads or touch sensor devices) are widely used in a variety of electronic systems. A proximity sensor device typically includes a sensing region, often demarked by a surface, in which the proximity sensor device determines the presence, location and/or motion of one or more input objects. Proximity sensor devices may be used to provide interfaces for the electronic system. For example, proximity sensor devices are often used as input devices for larger computing systems (such as opaque touchpads integrated in, or peripheral to, notebook or desktop computers). Proximity sensor devices are also often used in smaller computing systems (such as touch screens integrated in cellular phones).

BRIEF SUMMARY OF THE INVENTION

One embodiment described herein is an electronic device that includes a coil and a sensing circuit configured to generate an oscillating electrical signal on the coil for performing inductive sensing. The electronic device also includes a charging circuit configured to receive power from the coil while the coil is inductively coupled to an external charging device. The electronic device includes selection logic configured to selectively couple the coil to one of the sensing circuit and the charging circuit.

Another embodiment described herein is an integrated circuit that includes a sensing circuit configured to generate an oscillating electrical signal on a coil for performing inductive sensing and a charging circuit configured to receive power from the coil while the coil is inductively coupled to an external charging device. The integrated circuit also includes selection logic configured to selectively couple the coil to one of the sensing circuit and the charging circuit.

Another embodiment described herein is a method that includes coupling a coil to a sensing circuit, the sensing circuit generating an oscillating electrical signal on the coil for performing inductive sensing and coupling the coil to a charging circuit, the charging coil receiving power from the coil while the coil is inductively coupled to an external charging device.

BRIEF DESCRIPTION OF DRAWINGS

The preferred exemplary embodiment of the present invention will hereinafter be described in conjunction with the appended drawings, where like designations denote like elements, and.

Figure 1:
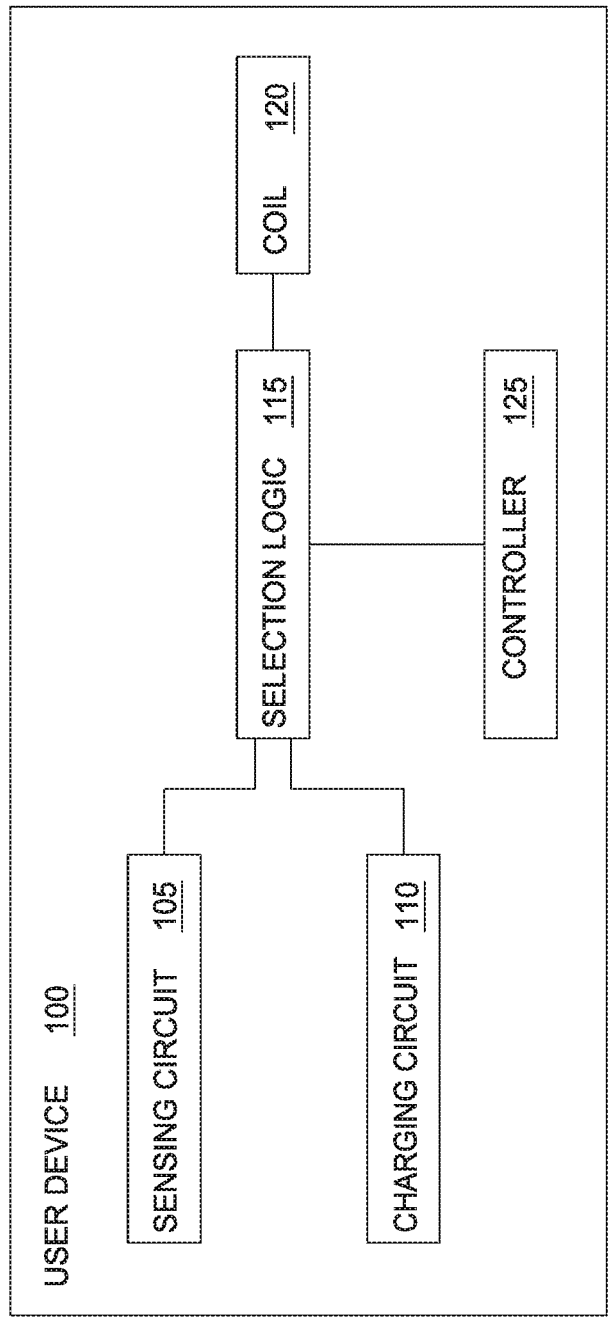
FIG. 1 is a block diagram of a user device containing a dual purpose coil in accordance with an embodiment of the invention.

To facilitate understanding, identical reference numerals have been used, where possible, to designate identical elements that are common to the figures. It is contemplated that elements disclosed in one embodiment may be beneficially utilized on other embodiments without specific recitation. The drawings referred to here should not be understood as being drawn to scale unless specifically noted. Also, the drawings are often simplified and details or components omitted for clarity of presentation and explanation. The drawings and discussion serve to explain principles discussed below, where like designations denote like elements.

DETAILED DESCRIPTION OF THE INVENTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Various embodiments of the present invention provide user devices and methods that facilitate improved usability. In one embodiment, the user device includes a dual purpose coil (or inductor) that is used when performing inductive sensing and when transferring electrical power to the user device. When performing inductive sensing, the user device couples the coil to a sensing circuit which measures a resistivity of a lossy material inductively coupled to the coil. In one embodiment, the user device may be worn on the wrist of the user so that the sensing circuit measures the resistivity corresponding to the flow of blood in an artery or vein. By monitoring changes in the resistivity of the blood or artery, the user device can identify the heartbeat of the user. When transferring electrical power, the user device couples the coil to a charging circuit which receives the power provided by an external charging device that is inductively coupled to the coil. The power can be used to charge a battery in the user device or power a component such as a display or speaker, among other devices.

FIG. 1 is a block diagram of a user device 100 containing a dual purpose coil 120 in accordance with an embodiment of the invention. The user device 100 broadly refers to any electronic device or system capable of electronically processing information. Some non-limiting examples of user devices 100 include personal computers of all sizes and shapes, such as desktop computers, laptop computers, netbook computers, tablets, web browsers, e-book readers, and personal digital assistants (PDAs). The user device 100 may be a communication device (including cellular phones, such as smart phones) or an information device such as a digital watch or a health monitoring device.

As shown, the user device 100 includes a sensing circuit 105, a charging circuit 110, selection logic 115, a coil 120, and a controller 125. The coil 120 is also referred to herein as a dual purpose coil since the coil 120 is used when performing two functions. Using control signals provided by the controller 125, the selection logic 115 selectively couples the coil 120 to either the sensing circuit 105 or to the charging circuit 110. When coupled to the sensing circuit 105, the coil 120 is used to perform inductive sensing of a material proximate to the user device 100. As used herein, inductive sensing generally includes measuring an attribute of a material proximate to the coil 120. In one embodiment, the sensing circuit 105 measures the resistivity of human tissue or blood in order to identify an attribute of the user or action performed by the user. For example, the device 100 may be a watch worn by the user so that the coil 120 is proximate to an artery or vein on the wrist of the user. In one embodiment, the coil 120 is disposed at a surface of the watch that contacts the skin of the user, or proximate to this surface (e.g., within 3-4 mm). Because the resistivity of the human tissues changes as the heart pumps blood through the artery or vein, the sensing circuit 105 can detect this change and identify a heartbeat or pulse of the user.

In another embodiment, the sensing circuit 105 detects changes in muscle tissue resistivity to identify a user action. For example, the device 100 may be health monitoring device worn on a chest of the user so that coil 120 and sensing circuit 105 measure changes in resistivity of muscles used when breathing. By monitoring these muscles over time, the user device 100 can determine a respiratory rate of the user. In another example, the user device 100 may be phone placed in a pocket of the user. The coil 120 may be disposed on or proximate to (e.g., within 3-4 mm) a back surface of the phone opposite a front surface of the phone that includes the display and touch interface. As the user moves, the separation distance between the coil 120 and the skin of the user may vary. Because the measured resistivity changes as this distance changes, the user device 100 can correlate changes in resistivity to user movement such as the user taking a step when walking or jogging. The user device 100 can use this information to log the number of steps the user takes or the amount of distance traveled by the user (assuming the average distance of the user's steps is known). In other embodiments, the user device 100 may use the resistivity measurements captured by the coil 120 and the sensing circuit 105 to determine a volume or velocity of a blood passing through magnetic flux generated by the coil 120. In this manner, the sensing circuit 105 and the coil 120 can identify a user attribute or action (e.g., heartbeat, pulse rate, respiratory rate, steps taken, etc.).

The coil 120 is also used to provide power to the user device 100. To do so, the controller 125 transmits control signals to the selection logic 115 which couple the charging circuit 110 to the coil 120. To receive the power, the coil 120 is inductively coupled to an external charging device which may include its own coil. Together, these coils function as a transformer and permit power to be transferred from the external charging device to the charging circuit 110. The charging circuit 110 can use this power to charge a battery and/or power a component in the user device 100—e.g., a display or speaker, among other devices. In this manner, the dual purpose coil 120 is used when performing inductive sensing and when transferring electrical power.

The controller 125 may be software, hardware, firmware, or some combination thereof. For example, the sensing circuit 105, charging circuit 110, and controller 125 may be part of the same integrated circuit or be formed using a multiple integrated circuits. Alternatively, the controller 125 may be a software application executed by a computing system in the user device 100.

Figure 2:
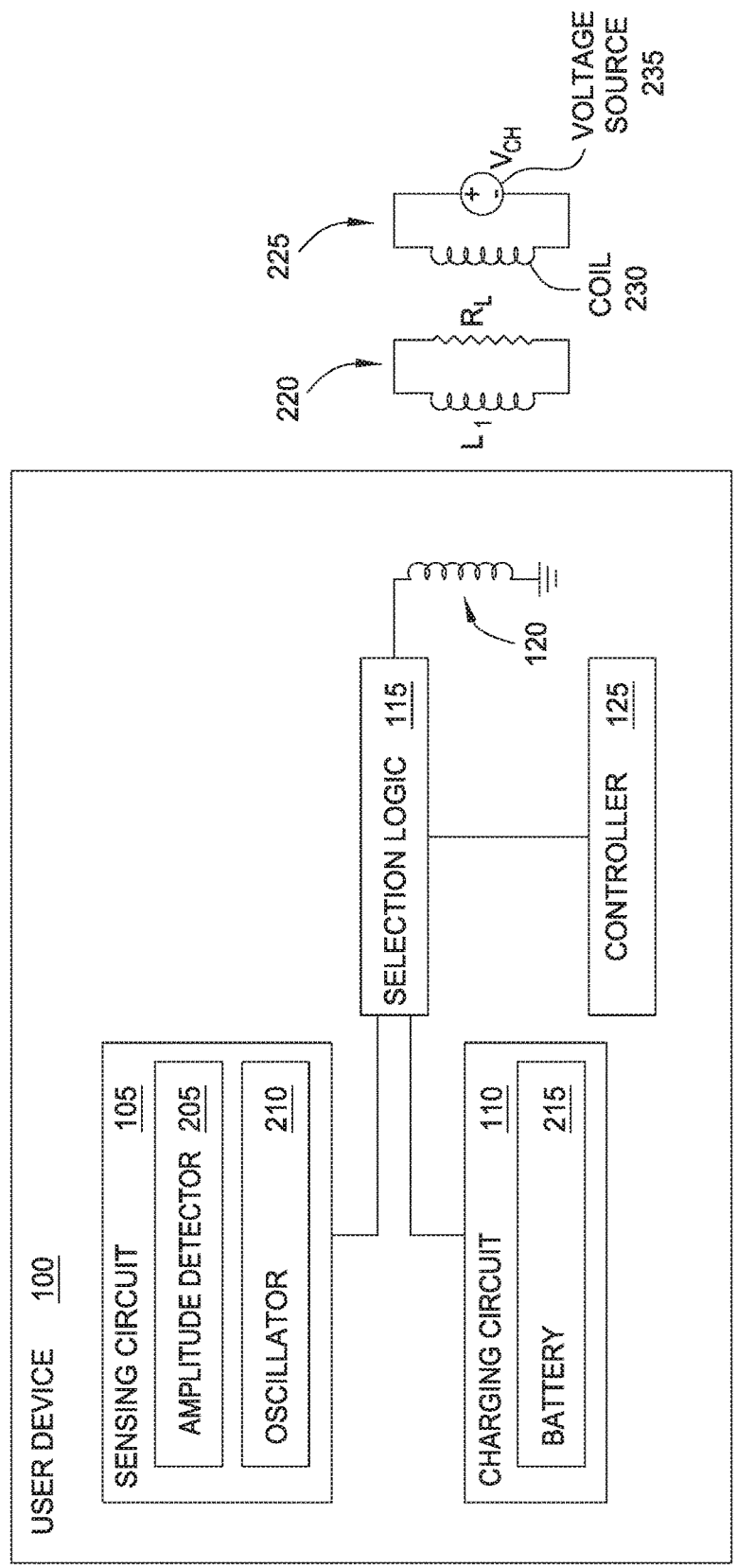
FIG. 2 is a block diagram of a user device containing a dual purpose coil in accordance with an embodiment of the invention.

FIG. 2 is a block diagram of the user device 100 containing a dual purpose coil 120 in accordance with an embodiment of the invention. In FIG. 2, the sensing circuit 105 includes an amplitude detector 205 and an oscillator 210. In one embodiment, the oscillator 210 generates an electrical signal that oscillates at a resonant frequency defined by the characteristics of the coil 120—i.e., the inductance of the coil 120. In one embodiment, the amplitude detector 205 is part of a feedback circuit for controlling a current source in the oscillator 210. When the coil 120 is coupled to a lossy material—e.g., human tissue or blood— this material reduces the amplitude of the oscillating electrical signal. The amplitude detector 205 identifies changes in the amplitude of the electrical signal and provides a feedback signal for the current source in the oscillator 210 which compensates for the lossy material.

FIG. 2 also illustrates two circuits 220 and 225 external to the user device 100. Circuit 220 represents the resistivity corresponding to a lossy material such as organic tissue or blood. Circuit 220 includes an inductance ($L_1$) and resistance ($R_L$) which represent the electrical properties of organic material. In a first mode of operation, the inductance $L_1$ in the circuit 220 is inductively coupled to the coil 120. As a result, the resistance $R_L$ reduces the amplitude of the electrical signal generated by the oscillator 210. The user device 100 can correlate the feedback signal generated by the amplitude detector 205 to a resistivity of the material— i.e., resistance $R_L$. This resistivity can then be correlated to a particular user attribute or action such as a heartbeat or step.

Circuit 225 represents an external charging device which can be inductively coupled to the coil 120 in a second mode of operation. In this mode, the controller 125 instructs the selection logic 115 to couple to the coil 120 to the charging circuit 110. When the coil 120 is inductively coupled to the coil 230, the charge voltage ($V_{CH}$) generated by the voltage source transfers power from the external charging device to the charging circuit 110. In this example, the transferred power is used to charge a battery 215. The controller 125 switches the user device 100 between the two different modes of operation so that the coil 120 can be used in both modes to couple the device 100 to an external material or device.

Figure 3:
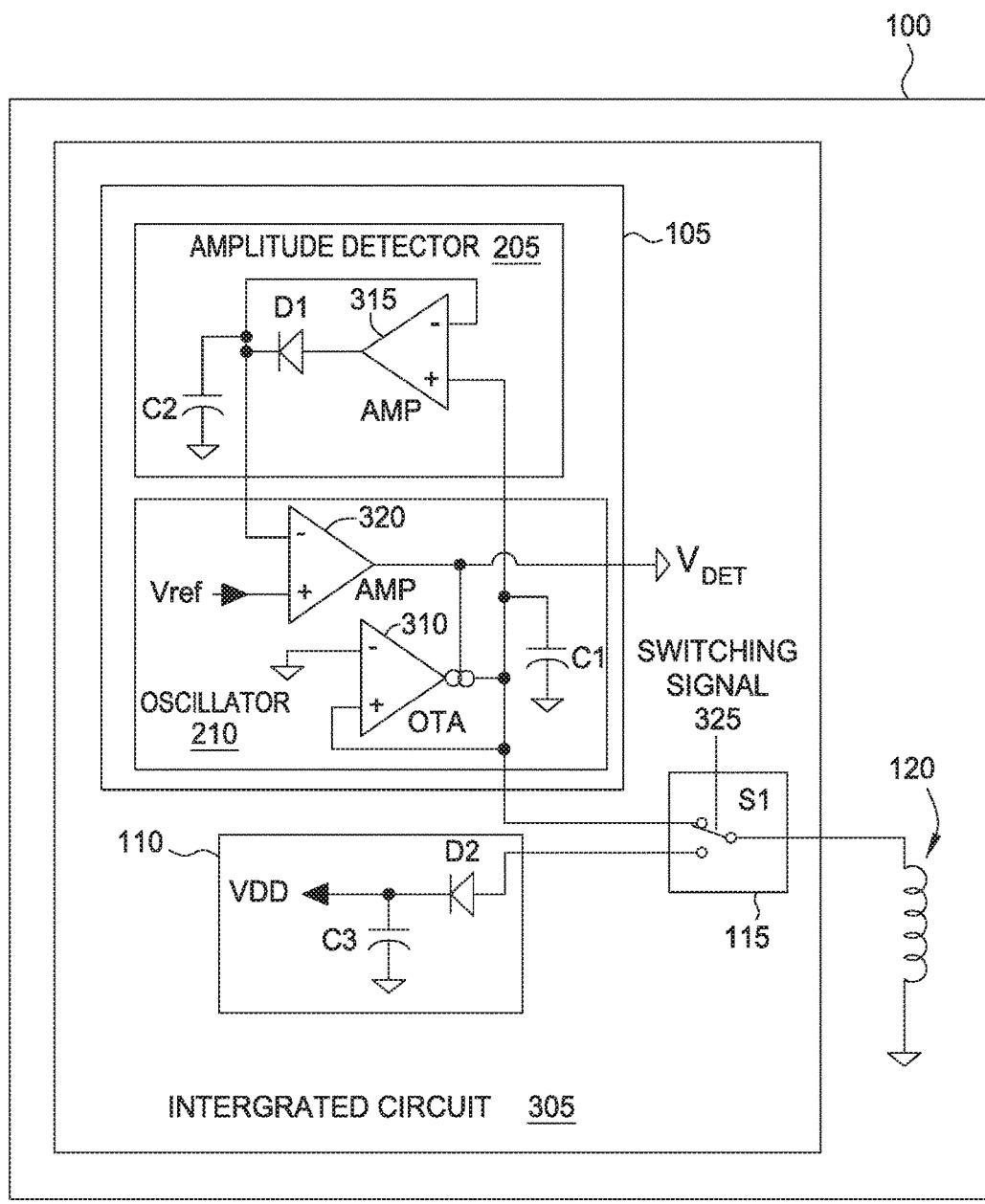
FIG. 3 is a circuit diagram of a user device in accordance with an embodiment of the invention.

FIG. 3 is a circuit diagram of the user device 100 in accordance with an embodiment of the invention. As shown, the user device 100 includes an integrated circuit 305 which contains the sensing circuit 105, the charging circuit 110, and the selection logic 115. Although shown here as being disposed on the same integrated circuit 305, in other embodiments, these components may be disposed on multiple integrated circuits.

In this embodiment, the selection logic 115 includes a switch $S_1$—e.g., one or more transistors—that selectively couples the coil 120 to either the sensing circuit 105 or the charging circuit 110. The oscillator 210 in the sensing circuit 105 includes an operational transconductance amplifier (OTA) 310, an amplifier 320, and capacitor $C_1$. In one embodiment, the capacitor $C_1$ and coil 120 (i.e., an inductor) function as an LC oscillator. When the coil 120 is inductively coupled to a lossy material (which is represented by circuit 220 in FIG. 2), the resistivity of this material affects the amplitude of the electrical signal generated by the oscillator 210.

The amplitude detector 205 detects changes in amplitude of the oscillating electrical signal. As shown, the amplitude detector 205 includes an amplifier 315, diode $D_1$, and capacitor $C_2$ which detect the amplitude changes. For example, during a heartbeat, the blood flow in an artery increases which changes the resistance $R_L$ shown in FIG. 2. This change in resistance causes a corresponding change in the amplitude of the electrical signal generated by the oscillator 210. In response, the output of the amplifier 315 (which is one of the inputs to amplifier 320) also changes to maintain the amplitude of the oscillating signal. Stated differently, the amplitude detector 205 outputs a signal that controls the gain of the oscillator 210 and increases or decreases the amplitude of the oscillating electrical signal. Moreover, the output of the amplifier 320 (i.e., $V_{DET}$) is used as the output of amplitude detector 205.

Although not shown in FIG. 3, the user device 100 may include a monitoring module coupled to the output of the amplitude detector 205 (i.e., $V_{DET}$) which detects changes in voltage or current. Because the changes in the output of the amplitude detector 205 correlate to the resistance $R_L$, the monitoring module can map these changes to a particular attribute such as a heartbeat, pulse rate, respiratory rate, blood flow, muscle density, etc. or a user action such as walking, jogging, etc. For example, if the resistance $R_L$ increases because of a surge in blood flow in an artery, the monitoring module can correlate an increase in the signal outputted by the amplitude detector 205 (in response to a decrease in the amplitude of the oscillating electrical signal) to a beginning of a heartbeat. Once the surge of blood flow has passed, the resistance $R_L$ decreases which causes a corresponding increase in the amplitude of the oscillating electrical signal and a reduction of the signal generated by the amplitude detector 205. The monitoring module can identify this reduction in the signal as an end of the heartbeat. By monitoring the change in the resistance $R_L$ over time, the monitoring module can identify a plurality of heartbeats, and thus, derive a pulse rate of the user.

A similar process may be performed for detecting respiratory rates or counting the number of steps taken by the user. For example, instead of monitoring the change of resistance caused by changes in blood flow, the sensing circuit 105 may monitor changes in resistance cause by muscles contracting or relaxing or changes in the separation distance between the coil 120 and the skin of the user. As the resistance $R_L$ increases and decreases, the monitoring module can identify these changes as the beginning and end of a particular user action. The monitoring module can be implemented using entirely hardware, entirely software, or some combination of hardware, software, or firmware.

Using switching signal 325, the controller can change the state of switch $S_1$, thereby coupling coil 120 to the charging circuit 110 rather than to the sensing circuit 105. For example, the controller may couple the switch $S_1$ to the coupling coil 120 in response to being put into a charging mode. For example, the user input device may include a wireless communication circuit (not shown) which detects the presence of the external charging device. For instance, the external charging device may include a RFID transmitter, while the user device 100 includes an RFID receiver. Once the RFID receiver successfully detects signals transmitted by the RFID transmitter, the controller switches the state of the switch S1 to couple the coil 120 to the charging circuit 110. In another embodiment, the sensing circuit 105 may include a power detection circuit for determining whether the external device applies a voltage across the coil 120. If so, the controller determines that the user has placed the device 100 on an external charging device, and in response, switches the state of the switch $S_1$ so that the coil 120 is coupled to the charging circuit 110.

Once coupled to the coil 120, the charging circuit 110 receives the charging voltage $V_{CH}$. This voltage can then be driven on the voltage network VDD which can be used to charge a battery or power one or more components in the user device 100. Once the coil 120 is no longer coupled to the external charging device, the controller may change the state of the switch $S_1$ so that the coil 120 is again electrically coupled to the sensing circuit 105.

Figure 4:
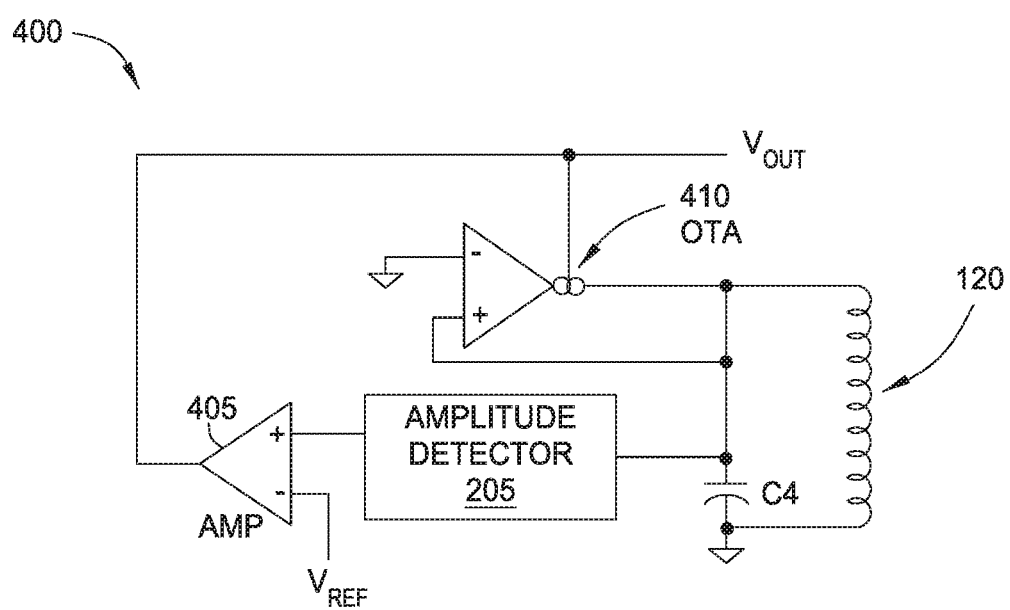
FIG. 4 is a diagram of sensing circuit for performing inductive sensing in accordance with an embodiment of the invention.

FIG. 4 is a diagram of sensing circuit 400 for inductive sensing in accordance with an embodiment of the invention. As shown, sensing circuit 400 illustrates a different circuit for performing inductive sensing than the sensing circuit 105 illustrated in FIG. 3. The sensing circuit 400 includes the amplitude detector 205, an amplifier 405, an OTA 410, and a capacitor $C_4$. Like above, the amplitude detector 205 identifies when the amplitude of an oscillating electrical signal generated by the OTA 410 changes. Using a feedback loop through the amplifier 405, the amplitude detector 205 outputs a control signal ($V_{OUT}$) which controls the gain of the OTA 410. $V_{OUT}$ may be used as an input to the monitoring circuit which correlates changes in the resistivity of the material to a user attribute or action. Alternatively, the monitoring circuit may correlate changes in $V_{OUT}$ to changes in the separation distance between the coil 120 and the skin of the user, thereby indicating user motion.

Figure 5:
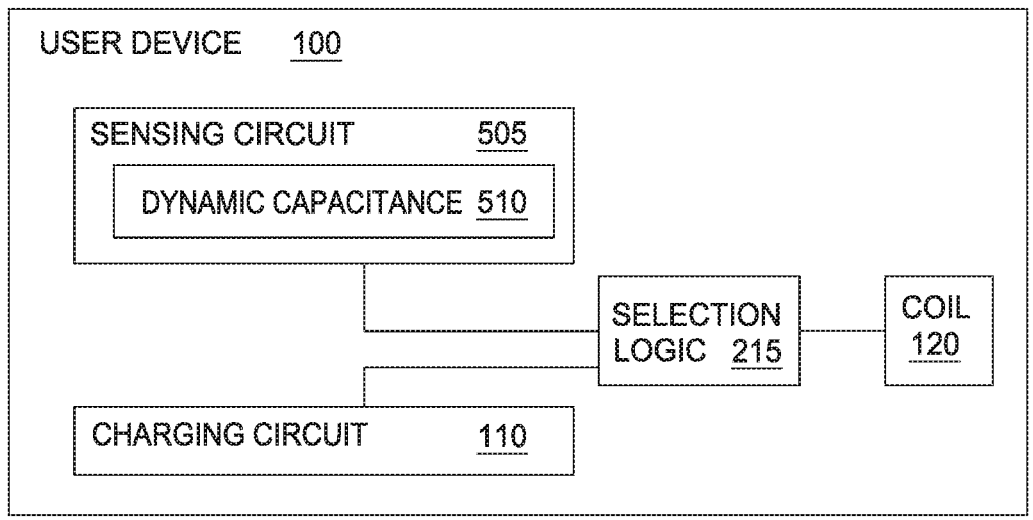
FIG. 5 is a block diagram of a user device for changing a measurement depth of inductive sensing in accordance with an embodiment of the invention.

FIG. 5 is a block diagram of the user device 100 for changing a depth of inductive sensing in accordance with an embodiment of the invention. As shown, the user device 100 includes a sensing circuit 505 with dynamic capacitance 510. In one embodiment, the sensing circuit 505 changes the dynamic capacitance 510 to alter the frequency at which the electrical signal generated by the sensing circuit 505 oscillates. For example, changing the dynamic capacitance 510 may change the frequency of a tank circuit used to determine the resonant frequency of the oscillator. In one embodiment, the sensing circuit 505 may use one or more switches to increase or decrease the dynamic capacitance 510. The sensing circuit 505 may have the same circuit layout as the sensing circuit 105 except for the addition of the dynamic capacitance 510 rather than a static capacitance.

Altering the frequency of the oscillating electrical signal using the dynamic capacitance 510 changes the depth of the inductive sensing. Generally, lowering the frequency of the oscillating electrical signal increases the depth of the measurement. Increasing the depth of the inductive measurement means the sensing circuit 505 measures the resistivity of a material that is further from the coil 120. For example, by changing the frequency, the sensing circuit 505 may switch from measuring the resistivity of tissue at the surface of the skin to measuring the resistivity of the tissue underneath the skin. In one embodiment, if the sensing circuit 505 is unable to detect a heartbeat, the circuit 505 may change the dynamic capacitance 510 to increase or decrease the depth of measurement to detect the heartbeat. For example, the sensing circuit 505 may use the dynamic capacitance 510 to increase the depth of measurement such that instead of measuring the resistivity of the epidermis, the circuit 505 measures the resistance of blood in an artery.

Figure 6:
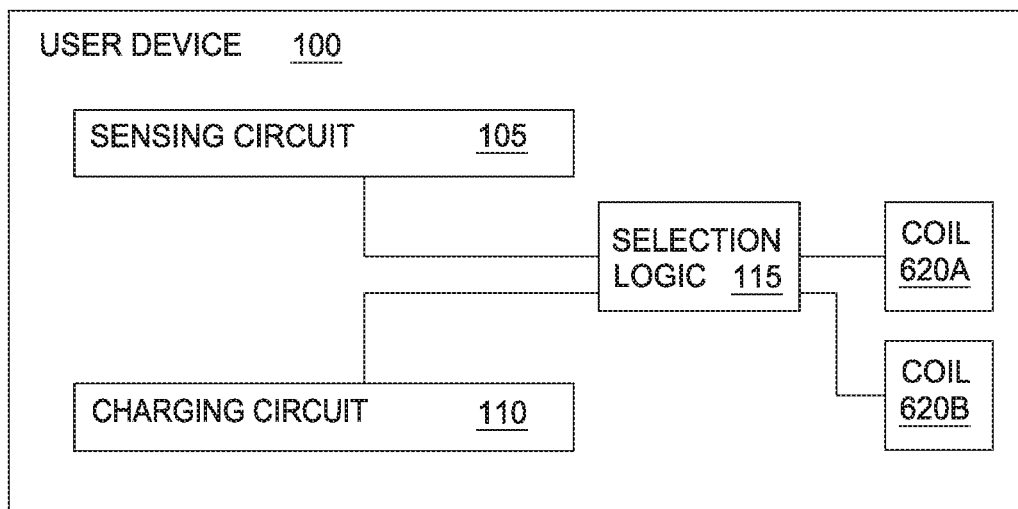
FIG. 6 is a block diagram of a user device containing a dual purpose coil and a sensing coil in accordance with an embodiment of the invention.

FIG. 6 is a block diagram of the user device 100 which contains a dual purpose coil 620A and a sensing coil 620B in accordance with an embodiment of the invention. In one embodiment, the dual purpose coil 620A is operated in the same manner as the coil 120 described above. That is, the selection logic 115 may selectively couple the coil 620A to either the sensing circuit 105 to perform inductive sensing or to the charging circuit 110 to provide power to the user device 100.

The selection logic 115 also can selectively couple the sensing coil 620B to the sensing circuit 105. Because the sensing coil 620B may have a different shape and/or diameter than coil 620A, the sensing coil 620B performs inductive sensing at a different depth or distance away from the user device 100 than coil 620A. Changing which of the coils 620 connects to the sensing circuit 105 determines the frequency of the oscillating signal by, for example, changing the inductance value of the tank circuit. As discussed above, changing the frequency of the oscillating signal changes the depth of measurement when performing inductive sensing.

In one embodiment, the coil 620A is used to sense the resistivity of tissue or blood at, or near, the surface of the skin, while the coil 620B is used to sense resistive of tissue or blood below the surface of the skin. Alternatively, in a scenario where the coils 620 may be further away from the user, the selection logic 115 may couple the coil 620B to the sensing circuit 105, for example, when the user device 100 is placed in a pocket where the device 100 can move freely rather than being strapped to the user.

In one embodiment, including a different coil (e.g., coil 620B) enables the user device 100 to effect greater changes in the depth of measurement than relying solely on the dynamic capacitance 510 as described in FIG. 5 to change the depth of measurement when performing inductive sensing. Stated differently, the shape and size of the coil 620B can be designed to cause a greater change in frequency, and thus, a greater change in the depth measurement, than changing capacitance in the sensing circuit 105. However, in one embodiment, the user device 100 may include both the sensing coil 620B as well as the dynamic capacitance 510. In this example, the user device 100 can achieve greater changes in the depth of measurement than using only one of these techniques alone. For example, when attempting to maximize the depth of measurement, the user device 100 switches to the coil 620 that provides the greatest depth of measurement as well as changes the dynamic capacitance to decrease the frequency of the oscillating signal.

Aspects of the present invention may take the form of an entirely hardware embodiment or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

The block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). It will also be noted that each block of the block diagrams, and combinations of blocks in the block diagrams, can be implemented by special purpose hardware-based systems that perform the specified functions or acts or carry out combinations of special purpose hardware and computer instructions.

Thus, the embodiments and examples set forth herein were presented in order to best explain the embodiments in accordance with the present technology and its particular application and to thereby enable those skilled in the art to make and use the present technology. However, those skilled in the art will recognize that the foregoing description and examples have been presented for the purposes of illustration and example only. The description as set forth is not intended to be exhaustive or to limit the disclosure to the precise form disclosed.

In view of the foregoing, the scope of the present disclosure is determined by the claims that follow.

We claim:

1. An electronic device, comprising:
   a coil;
   a sensing circuit configured to generate an oscillating electrical signal on the coil for performing inductive sensing;
   a charging circuit configured to receive power from the coil while the coil is inductively coupled to an external charging device; and
   selection logic configured to selectively couple the coil to one of the sensing circuit and the charging circuit.

2. The electronic device of claim 1, wherein the sensing circuit comprises:
   an amplitude detector configured to detect, and compensate for, changes in an amplitude of the oscillating electrical signal.

3. The electronic device of claim 2, further comprising a monitoring module configured to monitor an output of the amplitude detector and correlate the output to a user attribute or action.

4. The electronic device of claim 1, further comprising a battery, wherein the charging circuit is configured to charge the battery using the received power.

5. The electronic device of claim 1, wherein the electronic device is a watch, wherein the coil is located proximate to a surface of the watch configured to contact skin on a user.

6. The electronic device of claim 1, wherein the electronic device is a smart phone, wherein the coil is located proximate to a back surface of the smart phone that is opposite a front surface of the smart phone comprising a display and a touch interface of the smart phone.

7. The electronic device of claim 1, wherein the selection logic is configured to disconnect the coil from the charging circuit when the sensing circuit is performing inductive sensing and disconnect the coil from the sensing circuit when the charging circuit is receiving power from the external charging device.

8. The electronic device of claim 1, wherein the sensing circuit further comprises:
a dynamic capacitance configured to alter a frequency of the oscillating electrical signal, thereby changing a depth of measurement of the inductive sensing.

9. The electronic device of claim 1, further comprising:
a sensing coil comprising at least one of a different shape and a different diameter than the coil, wherein the selection logic is configured to selectively couple the sensing coil to the sensing circuit in order to change a depth of measurement of the inductive sensing relative to the depth of measurement when the coil is used to perform inductive sensing.

10. An integrated circuit, comprising:
a sensing circuit configured to generate an oscillating electrical signal on a coil for performing inductive sensing;
a charging circuit configured to receive power from the coil while the coil is inductively coupled to an external charging device; and
selection logic configured to selectively couple the coil to one of the sensing circuit and the charging circuit.

11. The integrated circuit of claim 10, wherein the sensing circuit comprises:
an amplitude detector configured to detect, and compensate for, changes in an amplitude of the oscillating electrical signal.

12. The integrated circuit of claim 11, further comprising a monitoring module configured to monitor an output of the amplitude detector and correlate the output to a user attribute or action.

13. The integrated circuit of claim 10, wherein the selection logic is configured to disconnect the coil from the charging circuit when the sensing circuit is performing inductive sensing and disconnect the coil from the sensing circuit when the charging circuit is receiving power from the external charging device.

14. The integrated circuit of claim 10, wherein the sensing circuit further comprises:
a dynamic capacitance configured to alter a frequency of the oscillating electrical signal, thereby changing a depth of measurement of the inductive sensing.

15. A method, comprising:
coupling a coil to a sensing circuit, the sensing circuit generating an oscillating electrical signal on the coil for performing inductive sensing; and
coupling the coil to a charging circuit, the charging circuit receiving power from the coil while the coil is inductively coupled to an external charging device.

16. The method of claim 15, wherein generating the oscillating electrical signal comprises:
detecting, using an amplitude detector, changes in an amplitude of the oscillating electrical signal resulting from the coil being inductively coupled to a lossy material.

17. The method of claim 16, further comprising:
monitoring an output of the amplitude detector; and correlating the output to a user attribute or action.

18. The method of claim 15, wherein coupling the coil to the sensing circuit comprises disconnecting the coil from the charging circuit, and wherein coupling the coil to the charging circuit comprises disconnecting sensing circuit from the coil.

19. The method of claim 15, further comprising:
altering a capacitance value in the sensing circuit to alter a frequency of the oscillating electrical signal, thereby changing a depth of measurement of the inductive sensing.

20. The method of claim 15, further comprising:
coupling a sensing coil to the sensing circuit, wherein the sensing coil comprises at least one of a different shape and a different diameter than the coil, wherein coupling the sensing coil to the sensing circuit changes a depth of measurement of the inductive sensing relative to the depth of measurement when the coil is used to perform inductive sensing.

* * * * *